US006288053B1

(12) United States Patent
Jirousek et al.

(10) Patent No.: US 6,288,053 B1
(45) Date of Patent: Sep. 11, 2001

(54) USE OF PROTEIN KINASE C INHIBITORS TO ENHANCE THE CLINICAL EFFICACY OF RADIATION THERAPY

(75) Inventors: Michael R. Jirousek; Lawrence E. Stramm; Douglas Kirk Ways, all of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/193,713

(22) Filed: Nov. 17, 1998

Related U.S. Application Data

(62) Division of application No. 08/841,738, filed on Apr. 30, 1997.
(60) Provisional application No. 60/016,658, filed on May 1, 1996.

(51) Int. Cl.⁷ .................. A61K 31/33; A61K 31/555; A61K 31/40
(52) U.S. Cl. .................. 514/183; 514/185; 514/410
(58) Field of Search .................. 514/183, 185, 514/410

(56) References Cited

U.S. PATENT DOCUMENTS

| | | |
|---|---|---|
| 4,937,232 | 6/1990 | Bell et al. . |
| 4,990,519 | 2/1991 | Jones et al. . |
| 5,057,614 | 10/1991 | Davis et al. . |
| 5,141,957 | 8/1992 | Jiang et al. . |
| 5,204,370 | 4/1993 | Jiang et al. . |
| 5,216,014 | 6/1993 | Jiang et al. . |
| 5,270,310 | 12/1993 | Bell et al. . |
| 5,461,146 | 10/1995 | Lewis et al. . |
| 5,481,003 | 1/1996 | Gillig et al. . |
| 5,488,167 | 1/1996 | Hudlicky . |
| 5,491,242 | 2/1996 | Gillig et al. . |
| 5,545,636 | 8/1996 | Heath, Jr. et al. . |
| 5,552,391 | 9/1996 | Coutts et al. . |
| 5,552,396 | 9/1996 | Heath, Jr. et al. . |
| 5,578,590 | 11/1996 | Grunicke et al. . |
| 5,616,577 | 4/1997 | Nambi et al. . |
| 5,621,098 | 4/1997 | Heath, Jr. et al. . |
| 5,621,101 | 4/1997 | Lewis et al. . |

FOREIGN PATENT DOCUMENTS 0 657 411 A1  2/1994  (EP) .

OTHER PUBLICATIONS

Bundgaard, H. *Design of Prodrugs*, (1985).
Vente, et al., *Cell Growth & Differentiation*, (1995), 6:371–382.
Ways, et al., *Cell Growth & Differentiation*, (1994), 5:1195–1203.
Barr et al., "Protein kinase C–β2 inhibits cycling and decreases c–myc–induced apoptosis in small cell lung cancer cells," *Cell Growth Differentiation 8*, 381–92, 1997.

*Primary Examiner*—Jerome D. Goldberg
(74) *Attorney, Agent, or Firm*—Paul R. Darkes

(57) ABSTRACT

A method for treating neoplasms is disclosed, particularly using the β-isozyme selective PKC inhibitor, (S)-3,4-[N,N'-1,1'-((2"-ethoxy)-3'''(O)-4'''-(N,N -dimethylamino)butane)-bis-(3,3'-indolyl)]-1(H)-pyrrole-2,5-dione or one of its salts, such PKC inhibitors enhance the clinical efficacy of oncolytic agents and radiation therapy.

3 Claims, 4 Drawing Sheets

• vehicle
■ 3nM Bryostatin 1
— 500 rads
--- 1000 rads

USE OF PROTEIN KINASE C INHIBITORS TO ENHANCE THE CLINICAL EFFICACY OF RADIATION THERAPY

This application claims the priority benefits of the U.S. Provisional application Ser. No. 60/016,658 filed May 1, 1996 which is a divisional of Ser. No. 08/841,738 filed Apr. 30, 1997.

BACKGROUND OF THE INVENTION

1. Field of the Invention

The present invention is broadly directed to a method for enhancing anti-neoplasm effects of chemotherapies and radiation therapies with PKC inhibitors. The present invention is particularly directed to the use of Protein Kinase C (PKC) inhibitors, especially a particular class of isozyme selective PKC inhibitors in combination with an oncolytic agent or γ-irradiation to enhance their anti-neoplasm effects in treatment of neoplasms.

2. Description of Related Art

Therapeutic treatments have been developed over the years to treat neoplasms. There are two major approaches to treat neoplasms: 1) chemotherapy employing oncolytic agents, and 2) radiation therapy, e.g., γ-irradiation. Oncolytic agents and γ-irradiation cause cytotoxic effects, preferentially to tumor cells, and cause cell death.

Studies have shown that γ-irradiation and certain groups of oncolytic agents assert their cytotoxic effects by activating programmed cell death or apoptosis. A balance between the activities of apoptotic and antiapoptotic intracellular signal transduction pathways is important towards a cell's decision of undergoing apoptosis in response to the above mentioned chemotherapy as well as radiation therapy.

PKC inhibitors has been proposed for cancer therapy, e.g. see U.S. Pat. No. 5,552,391, and PKC activities have been indicated to exert antiapoptotic effects, especially in response to radiation therapies, e.g., γ-irradiation. In particular, studies have shown that activation of PKC inhibits apoptosis induced by anti-neoplasmn agents such as Ara-c, 2-chloro-2-deoxyadenosine, 9-β-D-arabinosyl-2-fluoroadenine, and γ-irradiation therapy. There also have been indications that down regulation of PKC activities in tumor cells enhances apoptosis stimulated by oncolytic agents. PKC activation has been shown to attenuate γ-irradiation induced cell death.

There is a need in the art to develop therapeutic agents which enhance the apoptotic signal transduction pathways in cells and thereby enhance the clinical efficacy of oncolytic agents and radiation therapy.

SUMMARY OF INVENTION

It is an object of the invention to provide methods for treating a neoplasm.

It is another object of the invention to provide methods for enhancing an anti-neoplasm effect of an oncolytic agent.

It is still another object of the invention to provide methods for enhancing anti-neoplasm effects of radiation therapy.

These and other objects of the invention are provided by one or more of the embodiments described below.

In one embodiment of the invention there is provided a method for treating a neoplasm which comprises administrating to a mammal in need of such treatment an oncolytic agent or γ-irradiation in combination with a protein kinase C inhibitor.

In still another embodiment of the invention there is provided a method for enhancing an anti-neoplasm effect of chemotherapy and radiation therapy which comprises administrating a protein kinase C inhibitor in combination with said oncolytic agent or radiation therapy.

The present invention provides the art with a method for increasing apoptotic effects in cells and is thus effective in enhancing the anti-neoplasm effects of chemotherapies and radiation therapies.

DETAILED DESCRIPTION OF THE INVENTION

Figure 1:
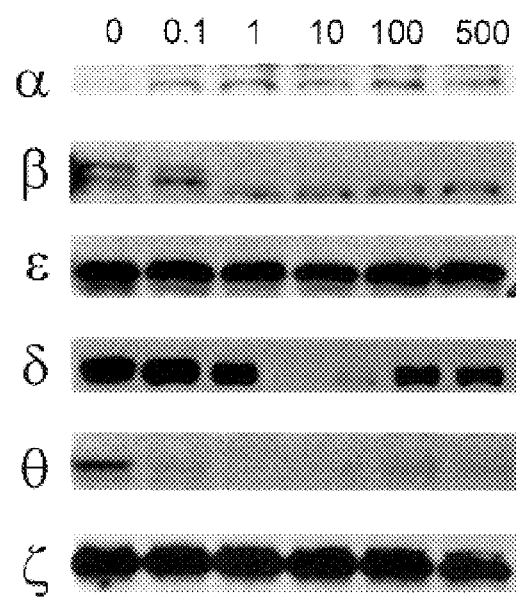
FIG. 1 shows the dosage effect of bryostatin 1 on PKC isoforms.

It is a discovery of the present invention that use of PKC inhibitors, especially a particular class of protein kinase C inhibitors, reduces or inhibits anti-apoptotic effects in a cell. Consequently, such compounds can be used to enhance the anti-neoplasm effects of chemotherapies and radiation therapies.

The method of this invention may employ any PKC inhibitor known in the art including non-specific PKC inhibitors and specific PKC inhibitors of different isoforms. Informations about PKC inhibitors, and methods for their preparation are readily available in the art. For example, different kinds of PKC inhibitors and their preparation are described in U.S. Pat. Nos. 5621101, 5621098, 5616577, 5578590, 5545636, 5491242, 5488167, 5481003, 5461146, 5270310, 5216014, 5204370, 5141957, 4990519, and 4937232, all of which are incoporated herein by reference. Preferably the present invention utilizes those protein kinase C inhibitors that effectively inhibit the β isozyme. One suitable group of compounds are generally described in the prior art as bis-indolylmaleimides or macrocyclic bis-indolylmaleimides. Bis-indolymaleimides well recognized in the prior art include those compounds described in U.S. Pat. Nos. 5621098, 5552396, 5545636, 5481003, 5491242, and 5057614, all incorporated by reference herein. Macrocyclic bis-indolylmaleimides are particularly represented by the compounds of formula I. These compounds, and methods for their preparation, have been disclosed in U.S. Pat. No. 5,552,396, which is incorporated herein by reference. In accordance with the present invention, these compounds are administered in combination with other anti-neoplasm therapies to a mammal in need of such treatment. In particular, these compounds can be used to enhance the anti-neoplasm effects of chemotherapies and radiation therapies.

One preferred class of compounds for use in the method of the invention has the formula:

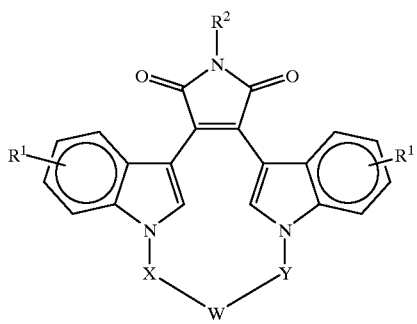

(I)

wherein:

W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$-C$_4$ alkylene, substituted alkylene, or together X, Y, and W combine to form —(CH$_2$)$_n$—AA—;

R$^1$s are hydrogen or up to four optional substituents independently selected from halo, C$_1$-C$_4$ alkyl, hydroxy, C$_1$-C$_4$ alkoxy, haloalkyl, nitro, NR$^4$R$^5$, or —NHCO(C$_1$-C$_4$ alkyl);

R$^2$ is hydrogen, CH$_3$CO—, NH$_2$, or hydroxy;

R$^3$ is hydrogen, (CH$_2$)$_m$aryl, C$_1$-C$_4$ alkyl, —COO(C$_1$-C$_4$ alkyl), —CONR$^4$R$^5$, —(C=NH)NH$_2$, —SO(C$_1$-C$_4$ alkyl), —SO$_2$ NR$^4$R$^5$), or —SO$_2$ (C$_1$-C$_4$ alkyl);

R$^4$ and R$^5$ are independently hydrogen, C$_1$-C$_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt, prodrug or ester thereof A more preferred class of compounds for use in this invention is represented by formula I wherein the moieties —X—W—Y— contain 4 to 8 atoms, which may be substituted or unsubstituted. Most preferably, the moieties —X—W—Y— contain 6 atoms.

Other preferred compounds for use in the method of this invention are those compounds of formula I wherein R$^1$ and R$^2$ are hydrogen; and W is a substituted alkylene, —O—, S—, —CONH—, —NHCO— or —NR$^3$—. Particularly preferred compounds are compounds of the formula Ia:

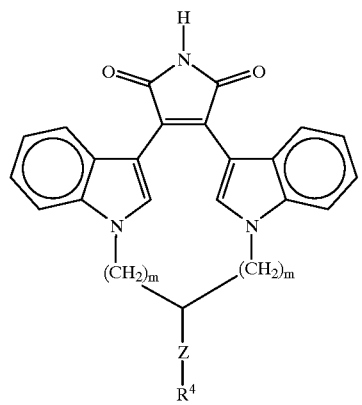

(Ia)

wherein Z is —(CH$_2$)$_p$— or —(CH$_2$)$_p$—O—(CH$_2$)$_p$—; R$^4$ is hydroxy, —SH, C$_1$-C$_4$ alkyl, (CH$_2$)$_m$aryl, —NH(aryl), —N(CH$_3$) (CF$_3$), —NH(CF$_3$), or —NR$^5$R$^6$; R$^5$ is hydrogen or C$_1$-C$_4$alky; R$^6$ is hydrogen, C$_1$-C$_4$ alkyl or benzyl; p is 0, 1, or 2; and m is independently 2 or 3, or a pharmaceutically acceptable salt, prodrug or ester thereof. Most preferred compounds of the formula Ia are those wherein Z is CH$_2$; and R$^4$ is —NH$_2$, —NH(CF$_3$), or —N(CH$_3$)$_2$.

Other preferred compounds for use in the method of the present invention are compounds wherein W in formula I is —O—, Y is a substituted alkylene, and X is an alkylene. These preferred compounds are represented by formula Ib:

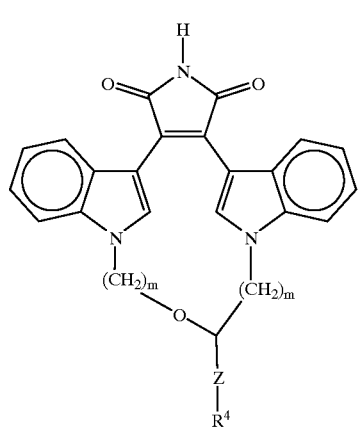

(Ib)

wherein Z is —(CH$_2$)$_p$; R$^4$ is —NR$^5$R$^6$, —NH(CF$_3$), or —N(CH$_3$) (CF$_3$); R$^5$ and R$^6$ are independently H or C$_1$-C$_4$ alkyl; p is 0, 1, or 2; and m is independently 2 or 3, or a pharmaceutically acceptable salt, prodrug or ester thereof. Most preferred compounds of formula Ib are those wherein p is 1; and R$^5$ and R$^6$ are methyl.

Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used.

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, *Design of Prodrugs*, (1985).

The synthesis of various bis-indole-N-maleimide derivatives is described in Davis el al. U.S. Pat. No. 5,057,614 and the synthesis of the preferred compounds suitable for use in this invention are described in the previously identified U.S. Pat. No. 5,552,396 and in Faul et al. EP publication 0 657 411 A1, all of which are incorporated herein by reference.

One particularly preferred protein kinase C inhibitor for use in the method of this invention is the compound described in Example 5 g ((S)-3,4[N,N'-1,1'-((2"-ethoxy)-3'"(O)-4'"-(N,N-dimethylamino)-butane)-bis-(3,3'-indolyl)]-1(H)-pyrrole-2,5-dione Hydrochloride Salt) of the aforementioned U.S. Pat. No. 5,552,396. This compound is a potent protein kinase C inhibitor. It is selective to protein kinase C over other kinases and is highly isozyme-selective, i.e., it is selective for the beta-1 and beta-2 isozymes. Other salts of this compound also would be favored, especially the mesylate salts.

A preferred mesylate salt can be prepared by reacting a compound of the formula II

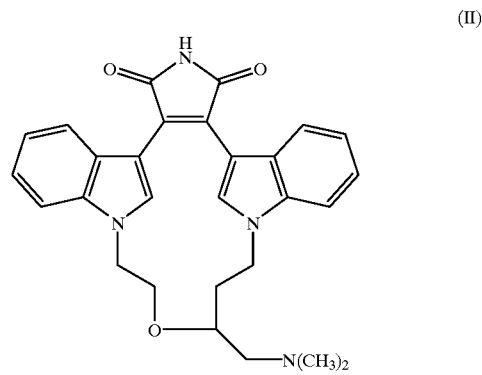

(II)

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction mixture is stirred until formation of the salt is complete, as determined by x-ray powder diffraction and can take from 5 minutes to 12 hours.

The salts of the present invention are preferably and readily prepared as a crystalline form. The trihydrate form of the salt may be readily converted to the monohydrate upon drying or exposure to 20–60% relative humidity. The salt is substantially crystalline demonstrating a defined melting point, birefringence, and an x-ray diffraction pattern. Generally, the crystals have less than 10% amorphous solid and preferably less than 5% and most preferably less than 1% amorphous solid.

The mesylate salt is isolated by filtration or other separation techniques appreciated in the art directly from the reaction mixture in yields ranging from 50% to 100%. Recrystallization and other purification techniques known in the art may be used to further purify the salt if desired.

The PKC inhibitors, including the compounds described above, are used in combination with conventional anti-neoplasm therapies to treat mammals, especially humans with neoplasia. The procedures for conventional anti-neoplasm therapies, including chemotherapies, e.g. using oncolytic agents and radiation therapies e.g., γ-irradiation are known, readily available, and routinely practiced in the art, e.g., see Harrison's PRINCIPLES OF INTERNAL MEDICINE 11th edition, McGraw-Hill Book Company.

Neoplasia is characterized by abnormal growth of cells which often results in the invasion of normal tissues, e.g., primary tumors or the spread to distant organs, e.g., metastasis. The treatment of any neoplasia by conventional anti-neoplasm therapies can be enhanced by the present invention. Such neoplastic growth includes but not limited to primary tumors, primary tumors that are incompletely removed by surgical techniques, primary tumors which have been adequately treated but which are at high risk to develop a metastatic disease subsequently, and an established metastatic disease.

Specifically, the PKC inhibitors described above can enhance the anti-neoplasm effects of an oncolytic agent. The wide variety of available oncolytic agents are contemplated for combination therapy in accordance with present invention. In a preferred embodiment, oncolytic agents that assert their cytotoxic effects by activating programed cell death or apoptosis are used in combination with the described PKC inhibitors. These include but not limited to 1-β-D-arabinofuranosylcytosine or Ara-c, etoposide or VP-16, cis-diamminedichloroplatinum (II) or cis-platinum, doxorubicin or adriamycin, 2-chloro-2-deoxyadenosine, 9-β-D-arabinosyl-2-fluoroadenine, and glucocorticoids.

All the neoplastic conditions treatable with such oncolytic agents can be treated in accordance with the present invention by using a combination of a PKC inhibitor with one or more oncolytic agents. The oncolytic agents assert the cytotoxicity or anti-neoplasm effects in a variety of specific neoplastic conditions. For example, Ara-c is normally used for treatment of childhood-null acute lymphoid leukemia (ALL), thymic ALL, B-cell ALL, acute myeloid leukemia, acute granulocytic leukemia and its variants, non-Hodgkins lymphoma, myelomonocytoid leukemia, acute megakaryocytoid leukemia and Burkitt's lymphoma, Adult-B-ALL, acute myeloid leukemia, chronic lymphoid leukemia, chronic myeloid leukemia, and T cell leukemia. VP-16 is normally used for treatment of testicular carcinoma, small and large non-small cell lung carcinoma, Hodgkin's lymphoma, non-Hodgkin's lymphoma, choriocarcinoma, Ewing's sarcoma, and acute granulocytic leukemia. Cis-platinum can be employed for treatment of testicular carcinoma, germ cell tumors, ovarian carcinomas, prostate cancer, lung cancer, sarcomas, cervical cancer, endometrial cancer, gastric cancer, breast cancer, and cancer of the head and neck. 2-Chloro-2-deoxyadenosine and 9-β-D-arabinosyl-2-fluoroadenine can be used to treat chronic lymphoid leukemia, lymphomas and hairy cell leukemia. Doxorubicin can be used to treat acute granulocytic leukemia and its variants, ALL, breast cancer, bladder cancer, ovarian cancer, thyroid cancer, lung cancer, Hodgkin's lymphoma, non-Hodgkin's lymphoma, sarcomas, gastric carcinoma, prostate cancer, endometrial cancer, Wilm's tumor and neuroblastoma Clinical effects of oncolytic agents in all neoplastic conditions treatable with oncolytic agents including the ones discussed above can be potentiated by use of a combination therapy with the identified PKC inhibitors in accordance with the present invention.

The PKC inhibitors identified in the present invention can also enhance the anti-neoplasm effects of a radiation therapy. Usually γ-irradiation is used to treat the site of a solid tumor directly.

Figure 2:
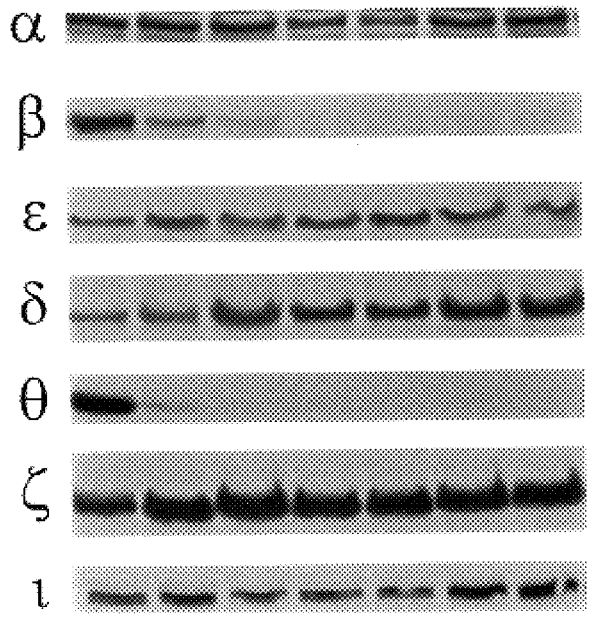
FIG. 2 demonstrates the incubation time effect of bryostatin 1 on PKC isoforms.
Figure 3:
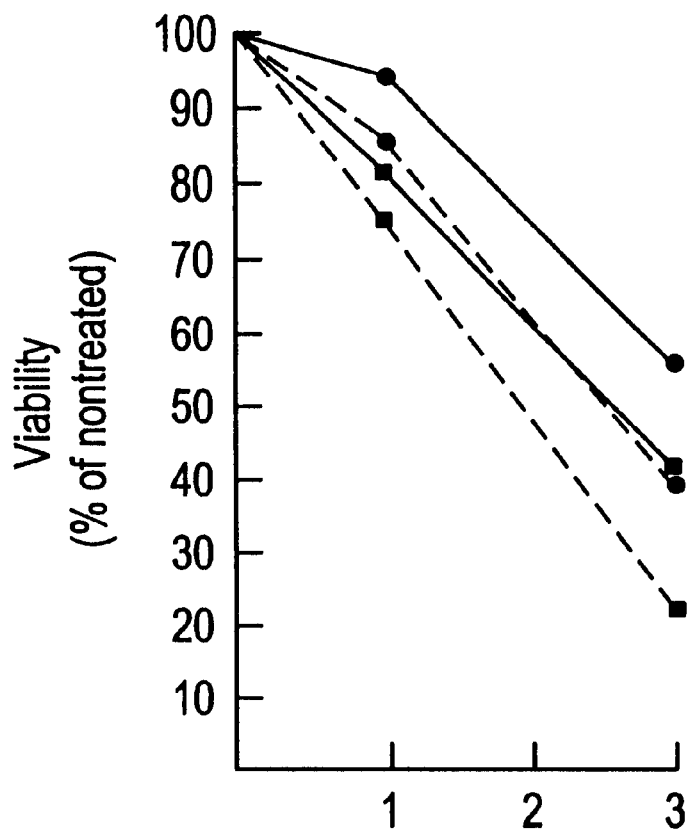
FIG. 3 demonstrates that down regulation of PKC-β enhances the efficacy of γ-irradiation.

Experimental results provided in the present invention demonstrate that the complete down regulation or loss of protein kinase C-β is associated with the synergistical enhancement of the oncolytic induced apoptosis in human leukemic cells (FIG. 1). Similarly, significant down regulation of protein kinase C-β in U937 human leukemic cells enhances radiation stimulated cell death (FIG. 2). U937 human leukemic cells that overexpress protein kinase C-β demonstrate resistance to radiation stimulated cell death (FIG. 3). These data provide a strong indication that the PKC inhibitors, especially β isozyme selective inhibitors, preferably used in accordance with the present invention can enhance tumor killing or the anti-neoplasm effects of chemotherapies and radiation therapies and improve clinical responses to these currently used therapeutic modalities.

The PKC inhibitors of the present invention are administered in combination with other anti-neoplasm therapies including oncolytic agents and radiation therapy. The phrase "in combination with other therapies" means that the compounds can be administered shortly before, shortly after, or concurrent with such other anti-neoplasm therapies. The compounds can be administered in combination with more than one anti-neoplasm therapy. In a preferred embodiment, the compounds are administered from 2 weeks to 1 day before any chemotherapy, or 2 weeks to 1 day before any radiation therapy. Alternatively, the PKC inhibitors can be administered during chemotherapies and radiation therapies. If administered following chemotherapy or radiation therapy, the PKC inhibitors should be given within 1 to 14 days following the primary treatments.

One skilled in the art will recognize that the amount of PKC inhibitor to be administered in accordance with the present invention in combination with other anti-neoplasm agents or therapies is that amount sufficient to enhance the anti-neoplasm effects of oncolytic agents or radiation therapies or that amount sufficient to induce apoptosis or cell death. Such amount may vary inter alia, depending upon the size and the type of neoplasia, the concentration of the compound in the therapeutic formulation, the specific anti-neoplasm agents used, the timing of the administration of the PKC inhibitors relative to the other therapies, and the age, size and condition of the patient.

Both in vivo and in vitro tests can be used to assess the amount of the compounds needed for inducing apoptosis. For example, human leukemic cells could be exposed in vitro to various concentrations of oncolytic agents, e.g., Ara-c, or to radiation in the presence or absence of the PKC inhibitor compounds used in the present invention Appropriate neoplastic cell types can be chosen for different oncolytic agents. Other protein kinase C selective inhibitors can also be used for comparison. At various time points, cells would be examined for viability by conventional methods or by any means available in the art. Apoptosis or cell death can be measured by any means known in the art. Cell death can be determined and quantified via trypan blue exclusion, and reduced clonogenecity in soft agar. As well understood by those skilled in the technology, apoptosis is a specific mode of cell death recognized by a characteristic pattern of morphological, biochemical, and molecular changes including but not limited to, endonucleolysis (DNA ladder), abnormal DNA breaks, and condensation of chromatin and cytoplasm (condensed and punctate nuclei). These changes can be readily detected by any means known in the art, e.g., microscopy; flow cytometric methods based on increased sensitivity of DNA to denaturation and altered light scattering properties; DNA fragmentation as assessed by agarose gel electrophoresis; terminal DNA transferase assay, (TdT assay), and nick translation assay (NT assay).

In vivo studies can be done using tumor xenografts inoculated into immunocompromised or sygenic animals. After inoculation and growth of the primary implant, the animals would be treated with the compounds in the present invention prior to exposure to the desired oncolytic or radiation treatment. The size of the tumor implant before and after each treatment in the presence and absence of the compounds in the present invention can be used as an indication of the therapeutic efficacy of the treatment Generally, an amount of protein kinase C inhibitor to be administered in combination with other anti-neoplasm therapies is decided on a case by case basis by the attending physician. As a guideline, the extent of the neoplasia, the body weight, and the age of the patient will be considered, among other factors, when setting an appropriate dose. Normally, the PKC inhibitors of the present invention are expected to potentiate the anti-neoplasm effects of oncolytic agents and radiation therapy from about 2 fold to about 10 fold.

Generally, a suitable dose is one that results in a concentration of the protein kinase C inhibitor at the site of tumor cells in the range of 0.5 nM to 200 μM, and more usually from 20 nM to 80 nM. It is expected that serum concentrations of 40 nM to 150 nM should be sufficient in most circumstances.

To obtain these treatment concentrations, a patient in need of treatment likely will be administered between about 0.1 mg per day per kg of body weight and 1.5 mg per day per kg. Usually, not more than about 1.0 mg per day per kg of body weight of protein kinase C inhibitor should be needed. As noted above, the above amounts may vary on a case-by-case basis.

The compounds of formula I and the preferred compounds of formula Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifing and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 64 mg of the active ingredient. However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifing agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon an affected tissue size and concentration of compound in the formulation. Generally, the formulation will be applied to the effected tissue in an amount affording from about 1 to about 500 μg compound per $cm^2$ of an affected tissue. Preferably, the applied amount of compound will range from about 30 to about 300 $μg/cm^2$, more preferably, from about 50 to about 200 $μg/cm^2$, and, most preferably, from about 60 to about 100 $μg/cm^2$.

The following formulation examples are illustrative only and are not intended to limit the scope of the invention in any way.

Formulation 1
Hard gelatin capsules are prepared using the following ingredients:

|  | Quantity (Mg/capsule) |
| --- | --- |
| Active agent | 250 |
| starch, dried | 200 |
| magnesium stearate | 10 |
| Total | 469 mg |

The above ingredients are mixed and filled into hard gelatin capsules in 460 mg quantities.

Formulation 2
A tablet is prepared using the ingredients below:

|  | Quantity (mg/capsule) |
| --- | --- |
| Active agent | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3
Tablets each containing 60 mg of active ingredient are made as follows:

|  | Quantity (mg/tablet) |
| --- | --- |
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLES

Example 1

Effects of Bryostatin to PKC Isoforms

This experiment demonstrates the dosage and time effects of bryostatin to PKC isoforms.

Human leukemia cells U937 in the amount of $0.5 \times 10^6$ were treated with various amount of bryostatin 1 for 24 hours. Subsequently, the cells were solubilized for preparation of protein samples according to a routine procedure. The protein samples from bryostatin treated cells were then used in Western blot analysis with a protein kinase C-β specific antiserum previously described in Ways et al., Cell Growth & Differentiation 1994, 5: 1195–1203. As shown in FIGS. 1 and 2, bryostatin treatment caused PKC-β activity to decrease within certain amount of time, i.e., 10 nM bryostatin affects PKC-β within 2 hours, or 1 nM bryostatin affects PKC-β within 24 hours. In a repeated experiment, similar results were obtained.

Example 2

The Enhanced Efficacy of γ-Irradiation Caused by PKC-β Down Regulation

This experiment demonstrates that PKC-β down regulation enhances the efficacy of γ-irradiation.

Human leukemia cells U937 were treated for 24 hours with either 3 nM bryostatin 1 or the control solution, i.e., the vehicle for bryostatin 1. The cells were then irradiated with either 500 or 1000 rads of γ-irradiation. Seventy-two hours after irradiation, cellular viability was examined using propidium iodide exclusion and quantified by FACS analysis as previously described in Ways et al., Cell Growth & Differentiation 1994, 5: 1195–1203. Viability assays were performed in triplicate. As shown in FIG. 3, γ-irradiation-induced apoptosis was enhanced under the condition when PKC-β was significantly down-regulated using bryostatin 1. Similar results were obtained in several repeated experiments.

Example 4

Figure 4:
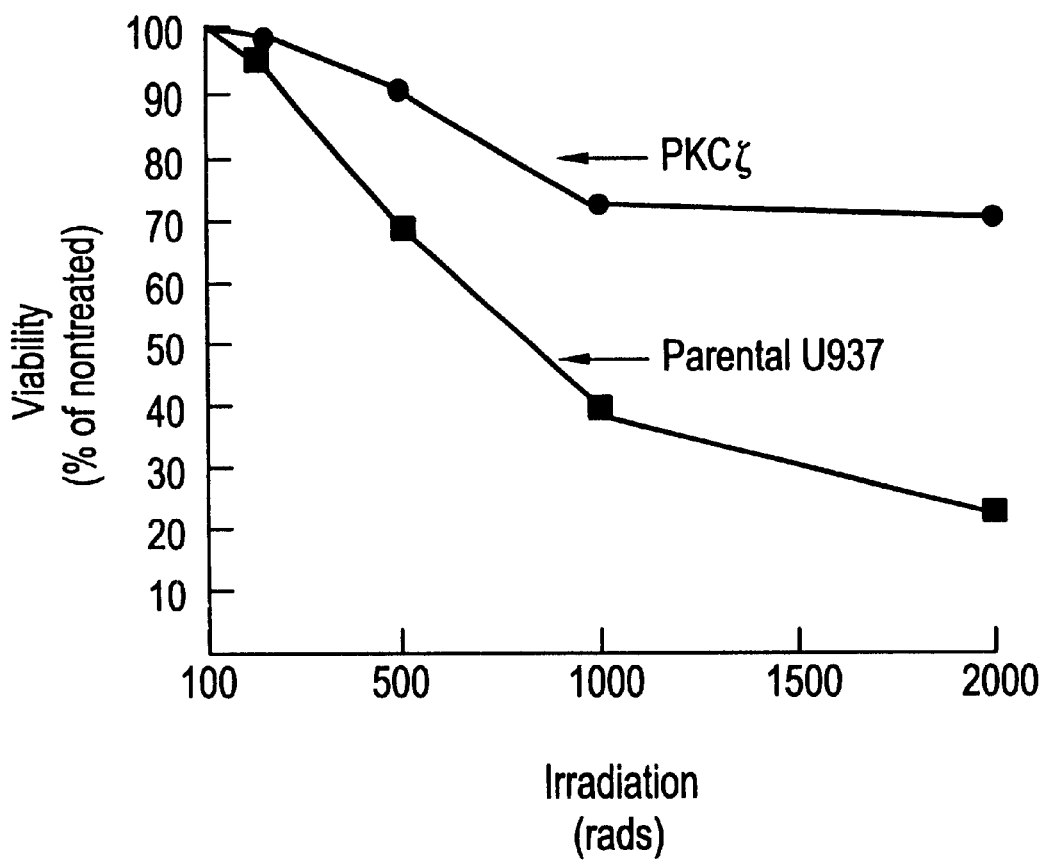
FIG. 4 shows that increased expression of PKC-β demonstrates resistance to radiation stimulated cell death.

Cells Overexpressing PKC-β Demonstrate Resistance to Radiation Stimulated Cell Death Parental U937 cells and U937 PKC-C overexpressing cells (PKC-ζ cells) were treated with 0, 500, or 1000 rads of γ-irradiation. It is known that PKC-ζ cells display increased level of PKC-β (Ways et al., Cell Growth & Differentiation, 1994, 5:1195–1203). Seventy two hours after irradiation, cellular viability was examined using propidium iodide exclusion and quantified by FACS analysis as previously described in Ways et al., Cell Growth & Differentiation, 1995, 6: 371–382. Viability assays were performed in triplicate. As shown in FIG. 4, cells having an increased level of PKC-β demonstrated resistance to radiation stimulated cell death. Similar results were obtained in several repeated experiments.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

What is claimed is:

1. A method for treating a neoplastic condition sensitive to the combination below which method comprises administering to a mammal, in need of such treatment, an effective amount of γ-irradiation having an anti-neoplastic effect in combination with a protein kinase C inhibitor of the formula

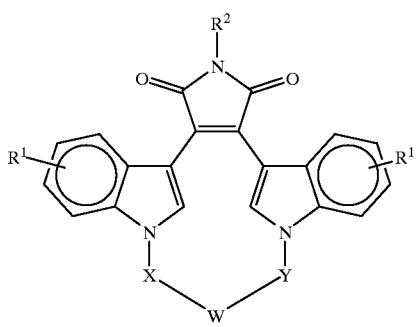

wherein:
- W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;
- X and Y are independently C$_1$–C$_4$ alkylene, substituted alkylene, or together X, Y, and W combine to form —(CH$_2$)$_n$—AA—;
- R$^1$s are hydrogen or up to four optional substituents independently selected from halo, C$_1$C$_4$ alkyl, hydroxy, C$_1$–C$_4$ alkoxy, haloalkyl, nitro, NR$^4$R$^5$, or —NHCO(C$_1$–C$_4$ alkyl);
- R$^2$ is hydrogen, CH$_3$CO—, NH$_2$, or hydroxy;
- R$^3$ is hydrogen, (CH$_2$)$_m$aryl, C$_1$–C$_4$ alkyl, —COO(C$_1$–C$_4$ alkyl), —CONR$^4$R$^5$, —(C=NH)NH$_2$, —SO(C$_1$–C$_4$ alkyl), —SO$_2$(NR$^4$R$^5$), or —SO$_2$(C$_1$–C$_4$ alkyl);
- R$^4$ and R$^5$ are independently hydrogen, C$_1$–C$_4$ alkyl, phenyl, benzyl, or combine to the nitrogen to which they are bonded to form a saturated or unsaturated 5 or 6 member ring;
- AA is an amino acid residue;
- m is independently 0, 1, 2, or 3; and
- n is independently 2, 3, 4, or 5, or a pharmaceutically acceptable salt, prodrug or ester thereof, and wherein the protein kinase C inhibitor is administered in an amount sufficient to enhance the anti-neoplastic effect of the γ-irradiation.

2. The method of claim 1 wherein the protein kinase C inhibitor has the following formula:

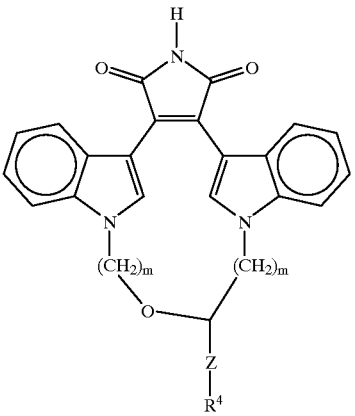

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof.

3. The method of claim 1 wherein the protein kinase C inhibitor comprises (S)-3,4-[N,N'-1,1'-((2''-ethoxy)-3'''(O)-4'''-(N,N-dimethylamino)-butane)-bis-(3,3'-indolyl)]-1(H)-pyrrole-2,5-dione or its pharmaceutically acceptable acid salt.

* * * * *